United States Patent [19]

Butler et al.

[11] 4,431,000
[45] Feb. 14, 1984

[54] TRANSCUTANEOUS NERVE STIMULATOR WITH PSEUSORANDOM PULSE GENERATOR

[75] Inventors: Russell B. Butler; Nancy A. Helm; A. Walter MacEachern, all of Littleton, Mass.

[73] Assignee: Gatron Corporation, Woburn, Mass.

[21] Appl. No.: 152,747

[22] Filed: May 23, 1980

Related U.S. Application Data

[63] Continuation-in-part of Ser. No. 964,560, Nov. 29, 1978, abandoned.

[51] Int. Cl.³ .............................................. A61N 1/36
[52] U.S. Cl. .................................................... 128/421
[58] Field of Search ................... 128/419 R, 421, 422, 128/423

[56] References Cited

U.S. PATENT DOCUMENTS

| | | | |
|---|---|---|---|
| 3,056,409 | 10/1962 | Edwards | 128/422 |
| 3,489,152 | 1/1970 | Barbara | 128/422 |
| 3,881,495 | 5/1975 | Pannozzo et al. | 128/422 |
| 3,954,111 | 5/1976 | Sato | 128/422 |
| 3,983,881 | 10/1976 | Wickham | 128/422 |
| 4,121,594 | 10/1978 | Miller et al. | 128/422 |
| 4,153,059 | 5/1979 | Fravel et al. | 128/422 |
| 4,338,945 | 7/1982 | Kosugi et al. | 128/421 |

*Primary Examiner*—William E. Kamm
*Attorney, Agent, or Firm*—Hamilton, Brook, Smith & Reynolds

[57] ABSTRACT

Aphasias and other neurologically based speech and language impairments are treated by means of a transcutaneous electrical nerve stimulator. Preferably an irregular pulse train is applied by means of a pseudorandom pulse generator to the stimulator electrodes. The trapezoidal, monophasic pulses mimic typical physiological wave forms and the average pulse rate is in the order of the alpha rate. A series of pulses has a zero DC level which enables the nerves to repolarize, and a current source in the stimulator reduces the effects of such variables as skin resistance. The base pulse rate, pulse width and pulse amplitude can be adjusted to meet the particular needs of a patient.

7 Claims, 5 Drawing Figures

TRANSCUTANEOUS NERVE STIMULATOR WITH PSEUSORANDOM PULSE GENERATOR

RELATED APPLICATION

This is a continuation in part of U.S. application Ser. No. 964,560, filed Nov. 29, 1978, now abandoned.

BACKGROUND OF THE INVENTION

This invention relates to a method and apparatus for treating a patient having a neurologically based speech and language impairment such as aphasia.

It is not uncommon that the victim of a neurological insult will subsequently suffer some speech and language impairment such as aphasia. Heretofore, patients with persistent aphasia have responded in varying degrees to a prolonged course of speech therapy. In 1955, several scientists suggested that loud auditory stimulation with strong kinesthetic stimulation were of some help in immediately improving speech in groups of adult stutterers and severe expressive aphasics. The results, however, were limited, and the strong vibrations which are irritating to both the patient and attendant may prove counterproductive.

An object of this invention is to provide a method and apparatus for treating a wide range of patients suffering from neurologically based speech and language impairments.

A further object of this invention is to provide such treatment by means of a low level stimulus which is readily acceptable to a patient.

SUMMARY

Electrical pulses are generated and are applied through the skin of the patient. To gain the most beneficial effect, the pulse train has a varying rate and is generated by a random pulse generator.

To further increase the effects of the speech treatment apparatus, each pulse is trapezoidal and monophasic to mimic the typical physiological wave forms, and the varying rate is in the order of the frequency of alpha waves.

To allow the nerves to repolarize, a set of pulses has a net zero DC level. Further, a current source overcomes the effects of such variables as skin resistance.

BRIEF DESCRIPTION OF THE DRAWINGS

The foregoing and other objects, features, and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DESCRIPTION OF PREFERRED EMBODIMENTS

Figure 1:
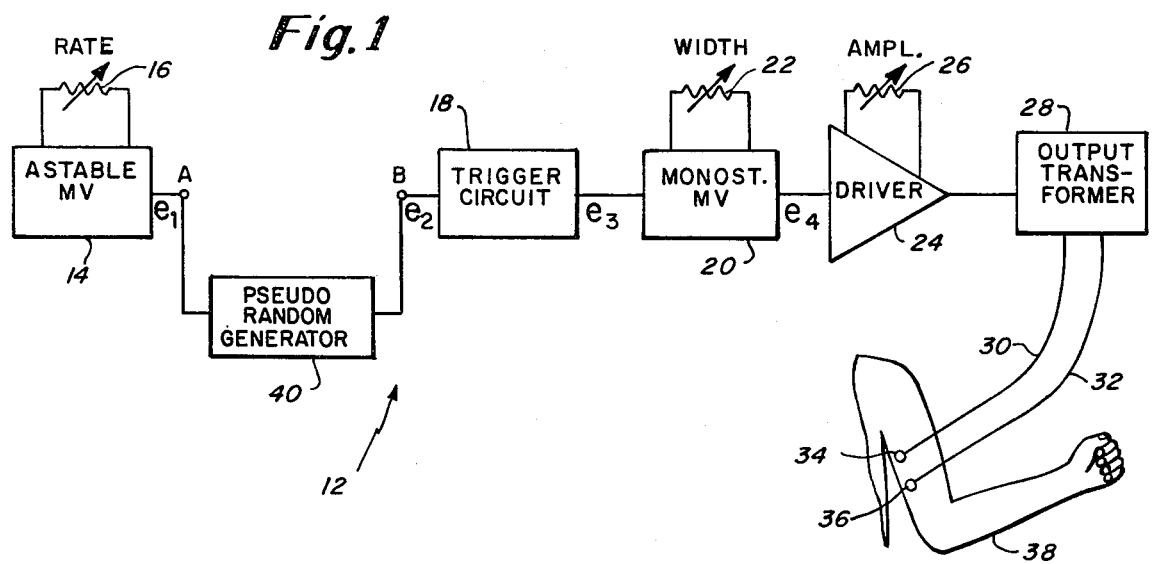
FIG. 1 is an electrical block schematic diagram of a transcutaneous nerve stimulator embodying the present invention and having electrodes attached to the arm of a patient.

A preferred transcutaneous nerve stimulator for use in practicing the present invention is shown in FIG. 1.

A clock signal for the stimulator is provided by an astable multivibrator 14. The multivibrator 14 provides a series of clock pulses $e_1$ (FIG. 2) at its output. The timing of those pulses, that is the periodicity of the pulse train, is variable and may be set by adjustment of a potentiometer 16 associated with the multivibrator.

In the conventional transcutaneous nerve stimulator, the clocking signal $e_1$ is delivered from pin A to pin B. Pin B is at the input of a trigger circuit 18. The trigger circuit is a differentiator which provides a sharp negative pulse with each falling edge of the clock signal. The negative pulses are applied to a monostable multivibrator 20. The multivibrator 20 sets the width of the pulses ultimately applied to the patient. Pulse width adjustment is by means of a width potentiometer 22. Typically the pulse width is variable between 50 and 500 microseconds.

In the conventional stimulator, the output $e_4$ of the monostable multivibrator is a constant frequency pulse train, each pulse of that train being of a predetermined pulse width. The pulse train is applied to a driver circuit 24 which is associated with an amplitude potentiometer 26. The potentiometer 26 sets the current level of the pulses applied through the output transformer 28 to output leads 30 and 32. The leads 30 and 32 lead to electrodes 34 and 36 which are either held against the skin of a patient or fixed to the skin by an adhesive or the like.

The transcutaneous nerve stimulator thus far described, having a constant rate ouput of variable frequency, has been widely used in the treatment of pain. In attempting to use the device in treating aphasia, limited beneficial results were obtained.

In accordance with a preferred embodiment, an electronic random pulse generator 40 is connected between the clocking astable multivibrator 14 and trigger circuit 18. The pulse generator 40, driven by a constant rate pulse train from the multivibrator 14, generates random, or more properly pseudorandom pulses $e_2$ which are applied to the conventional trigger circuit 18. The term random is used loosely. It should be apparent to one skilled in electronics that a truly random generator would not be feasible in an application such as this. Rather, a pseudorandom generator, one which repeats itself after some predetermined relatively lengthy period of time, is used. Over that predetermined length of time, which in the present case is in the order of minutes, a pattern is established. But, the pulse rate can be said to be constantly varying within the pattern because no three pulses establish a rate.

The trigger circuit 18 is not affected by the randomness of the signal $e_2$. It still provides a negative pulse with each falling edge at its input. The resulting train of negative pulses $e_3$ is also random. The random negative pulses initiate pulses of predetermined pulse width to provide the random pulse train $e_4$. Those pulses are then amplified and shaped through the driver 24 and the transformer 28 to provide a train of shaped, random pulses across the leads 30 and 32.

Figure 2:
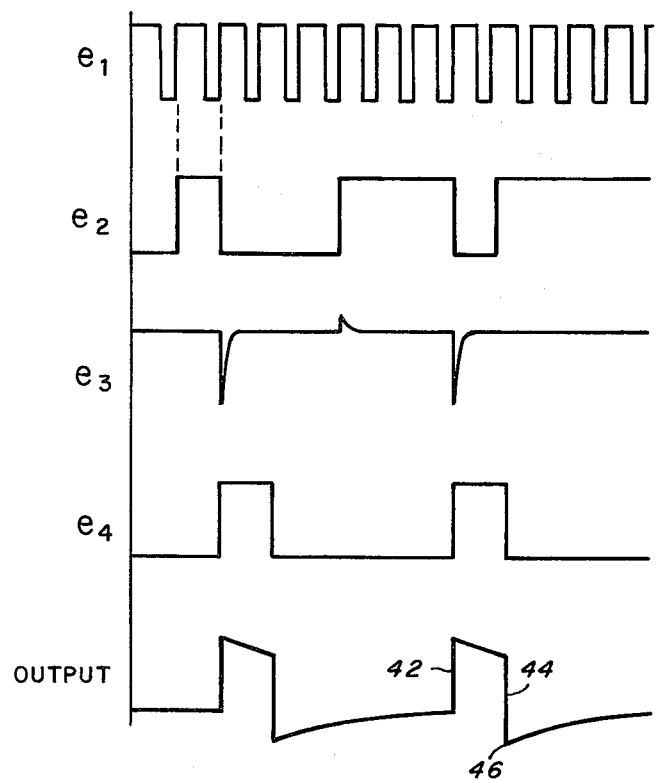
FIG. 2 is a timing chart of five voltages in the circuit of FIG. 1.

The particular shape of the random output pulses shown in FIG. 2 is a shape used in pain control and that shape has been found to be particularly suitable for use in treating speech and language impairments. Each pulse is generally trapezoidal in that the pulse is not level but decays slightly from the leading edge 42 to the falling edge 44. Also, the falling edge of the pulse drops below the zero DC level as at 46. This begins a trailing portion or after-potential of the signal. The after-potential gradually returns to the zero DC level before a subsequent pulse is initiated. Such a train of pulses closely mimics the typical physiological wave forms of the body. To further relate the output pulses to the physiological waves, the base rate of the pulse train, that is the clock frequency of signal $e_1$, is in the order of the alpha rate. The alpha rate is about 14 cycles per second and the astable multivibrator generates a clock signal in the range of about 3.5–35 hertz.

By properly setting the time between pulses at some length of time greater than the pulse width, the cells in the body are permitted to repolarize with the after-potential after each electrical pulse. The signal shown in FIG. 2 is monophasic; that is only the positive going portion of the signal has a sufficient magnitude to trigger the physiological response. Thus, a time greater than the pulse width must be provided between pulses to repolarize the cells.

It is believed that by applying an electrical pulse train to any portion of the body, the pulses are transmitted to the central nervous system, producing neurotransmitters, and result in inhibition of the distorted facilitation resulting from the neurologic dysfunction.

Unfortunately, in at least one patient it was found that the body somehow accomodated to a continuous series of pulses and the beneficial effect of the electrical stimulus was lost. In accordance with this preferred embodiment, generally rectangular pulses are applied randomly, or at least at such a varying rate that the body does not accomodate to the signals, and the brain continues to respond to the electrical impulses.

Figure 3:
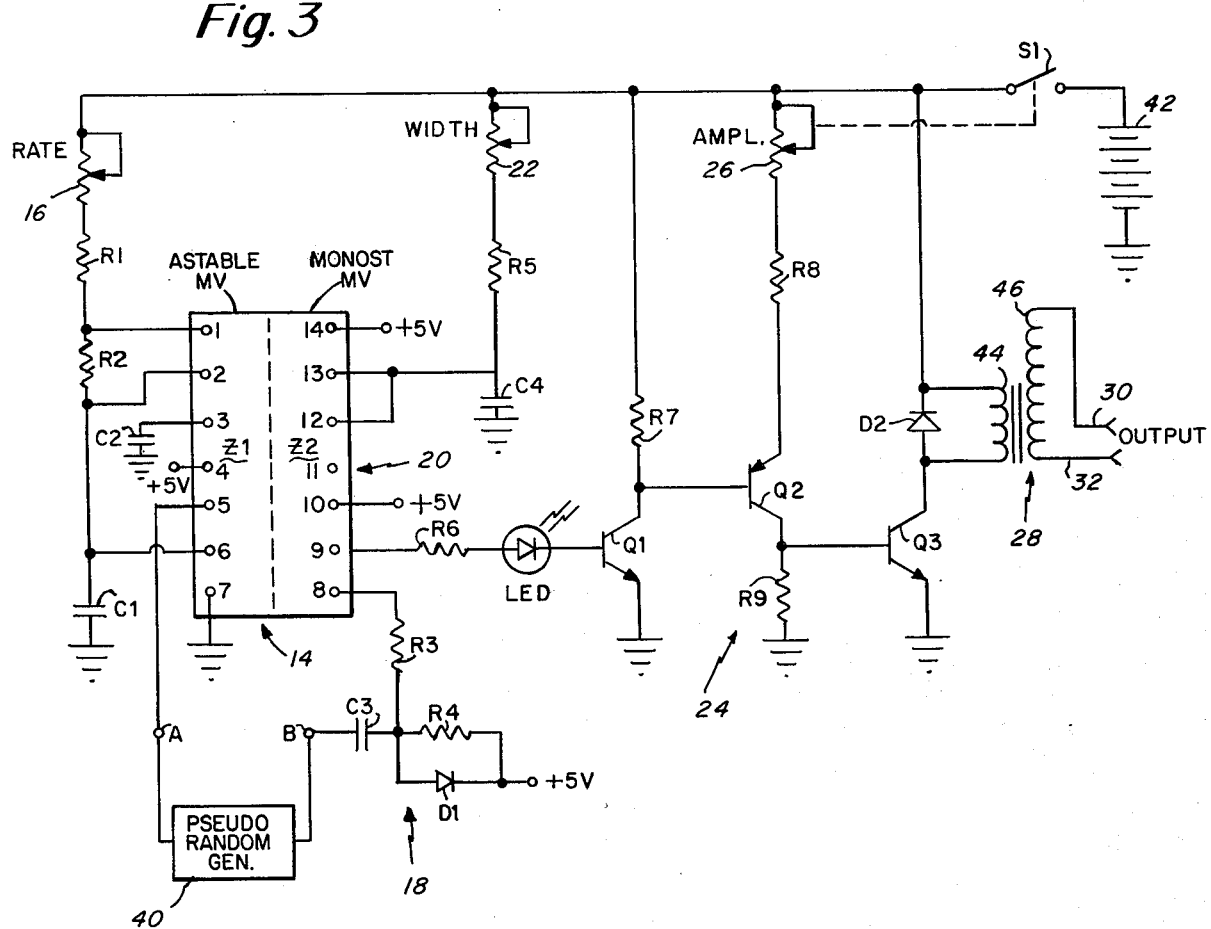
FIG. 3 is a detailed electrical schematic of that portion of the transcutaneous nerve stimulator of FIG. 1 used in a conventional device.
Figure 4:
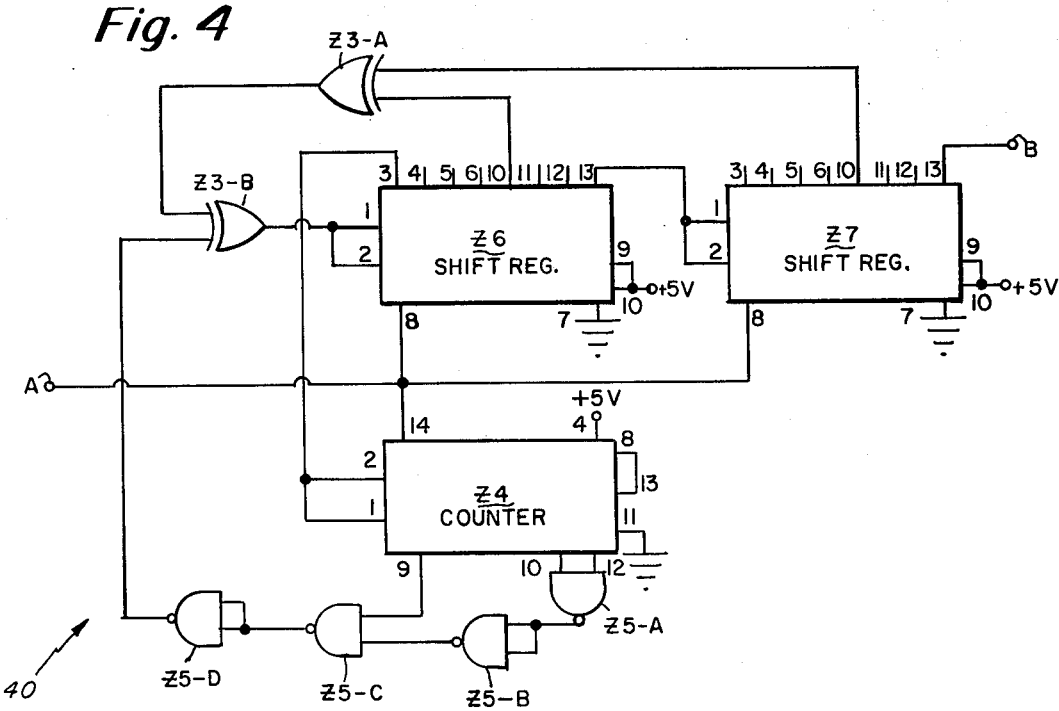
FIG. 4 is a detailed schematic of a possible pseudo-random pulse generator to be used in the transcutaneous nerve stimulator of FIG. 1.

The specific circuitry used in the embodiment of FIG. 1 is shown in FIGS. 3 and 4. FIG. 3 shows the detailed electronic circuitry of a conventional transcutaneous nerve stimulator; and a random pulse generator is shown in block form. That stimulator, without the random generator, has been sold by Gatron Corporation since 1974. FIG. 4 shows a conventional pseudorandom pulse generator suitable for use in the circuit of FIG. 3.

The circuit of FIG. 3 operates as follows. A five volt reference is applied from the battery 42 through an on/off switch S1 to each stage of the circuit. In the astable multivibrator stage the five volts is applied across a rate adjusting potentiometer 16, resistors R1 and R2, and a capacitor C1 to ground. Those circuit elements are connected to pins 1, 2 and 6 of the freerunning astable multivibrator portion Z1 of an integrated circuit element. The integrated circuit is an XR556CP. A stable voltage, provided across capacitor C2, is compared to the voltage across capacitor C1 as the latter charges. The charging time of capacitor C1 is determined by the potentiometer 16. After capacitor C1 has charged to the level of capacitor C2, a negative going two millisecond pulse is supplied on pin 5 and capacitor C1 is discharged. Thus, a series of pulses is supplied to pin 5 and pin A, and the timing of the pulse train is determined by the RC time constant of resistors 16, R1 and R2 and capacitor C1.

The clock signal from pin A is applied through the pseudorandom generator 40 to provide a pseudorandom pulse train on pin B.

The pulses at pin B are applied through the differentiating trigger circuit 18 which includes the capacitor C3, and resistors R3 and R4. A diode D1 provides clamping of positive going signals. A sharp negative pulse from the trigger circuit is applied to pin 8 of the monostable multivibrator portion Z2 of the integrated circuit XR556CP.

A negative pulse from the trigger circuit 18 triggers the monstable multivibrator 20 to provide a pulse on pin 9. Pins 12 and 13 are opened to allow the capacitor C4 to charge. The charging time of capacitor C4 is determined by the width potentiometer 22 and resistance R5. When the potential across capacitor C4 compares with an internal reference voltage, the charging cycle is terminated and capacitor C4 discharges. The output pulse on output pin 9 then returns low. Thus, a high output pulse $e_4$ is provided at pin 9 of the monostable multivibrator 20 during the charging time of capacitor C4.

The pulse from the monostable multivibrator 20 is applied through a current limiting resistor R6 and a light emitting diode LED to the base of transistor Q1. With the pulse, the LED and transistor turn on and current is drawn through resistor R7. The resulting low voltage at the collector of transistor Q1 turns transistor Q2 on to draw current through the amplitude adjusting potentiometer 26 and resistor R8. The emitter resistors R8 and 26 establish the current flow through the pnp transistor Q2.

Most of the current flowing through transistor Q2 is directed through the base of transistor Q3. Resistor R9 is a large resistor which allows discharge of the charge on the base of transistor Q3 when transistor Q2 is eventually turned off. Thus, resistor R9 decreases turn off time of transistor Q3 and reduces pulse fall time at the Q3 base.

With current flowing through transistor Q3 during a pulse of signal $e_4$, current is drawn through the primary 44 of transformer 28. The current flowing through transistor Q3 is determined by the product of the transistor beta and the input base current, and the input base current is determined by the potentiometer 26. The current pulses through the primary 44 are transferred through the secondary 46 by a one-to-fifteen turn ratio. The high output impedance of the transformer causes it to appear as a constant current source to normal loads, and the transformer circuit provides the wave shaping of the output pulses shown in FIG. 2. A diode D2 provides a path for quenching of primary current when transistor Q3 turns off after a pulse signal $e_4$.

The following values have been found suitable for the above described circuit elements:

Potentiometers 16, 22: 1 M ohm
Potentiometer 26: 5 K ohm
R1, R2: 33 K ohm
R3, R4: 10 K ohm
R5: 100 K ohm
R6: 10 ohm
R8: 68 ohm
R7, R9: 10 K ohm
C1: 0.4 µf
C2: 4.7 µf
C3: 0.01 µf C4: 390 pf To provide a pseudorandom pulse train, the circuit of FIG. 4 is connected between pins A and B in the conventional circuit of FIG. 3. The circuit of FIG. 4 is itself a conventional pseudorandom pulse generator. The shift registers Z6 and Z7 are 74C164 circuits and the counter Z4 is a 74C93.

Each clock signal applied to pin A is applied to the clock inputs of both the counter Z4 and the shift registers Z6, Z7. Assume the shift registers Z6 and Z7, connected in series, to be cleared. The counter counts up from zero until the logic circuitry Z5 detects a count to 14 indicated by a high output on each of pins 9, 10 and 12 from the counter. The count to 14 is then carried as a high input to the exclusive OR gate Z3B at the input to shift register Z6. The exclusive OR applies a pulse to register Z6 and the pulse is shifted through Z6 and Z7 with each subsequent clock pulse received from pin A. With the shift of the pulse to pin 3, the counter Z4 is reset and it once again begins to count to 14.

Once the first pulse input to shift register Z6 is shifted to pin 10, a signal is fed through exclusive OR gate Z3A to gate Z3B. Thus, a second pulse is read into the shift register and that pulse is shifted with subsequent clock signals from pin A. When shifted to pin 3 the pulse from pin 10, through gate Z3A and Z3B, also resets the counter. At the same time, the initial pulse continues to shift through the dual register Z6, Z7.

Similarly, a bit shifted to pin 10 of register Z7 starts a new bit through the shift registers as it continues to the output pin B. However, where pin 10 of Z6 and pin 10 of Z7 are both high simultaneously, no additional pulse will be read into the shift register. Any bit fed back to the input gate Z3B, when shifted to pin 3, resets the counter Z4. In this manner, a pseudorandom train of pulses shifted through the shift registers is generated at output pin B.

It will be noted that counter Z4 only counts to 14 when there has been a continuous lack of feedback through gate Z3A. At that point in the operation of the pseudorandom pulse generator, after about a minute or more in the usual case, all zeros occur at the Z6, Z7 outputs and the counter is permitted to count to 14. The counter thus provides an input to gate Z3B to recycle the pseudorandom pulse train.

As noted above, in the preferred embodiment the base frequency of signal $e_1$ is in the order of the alpha wave frequency of 14 cycles per second. The astable multivibrator 14 has been designed to have a frequency range of about 3.5 to 35 hertz. Although it is preferred that this low frequency range be used, much higher frequencies, for example up to 180 hertz, may be used.

Although for treatment of pain, the usual transcutaneous nerve stimulator has a current output from 10 to 60 milliamps, to treat aphasia and the like only about five milliamps is required. The current level could go much higher but this minimum level of about five milliamps is preferred. The circuit disclosed offers a range of two to sixty milliamps.

Figure 5:
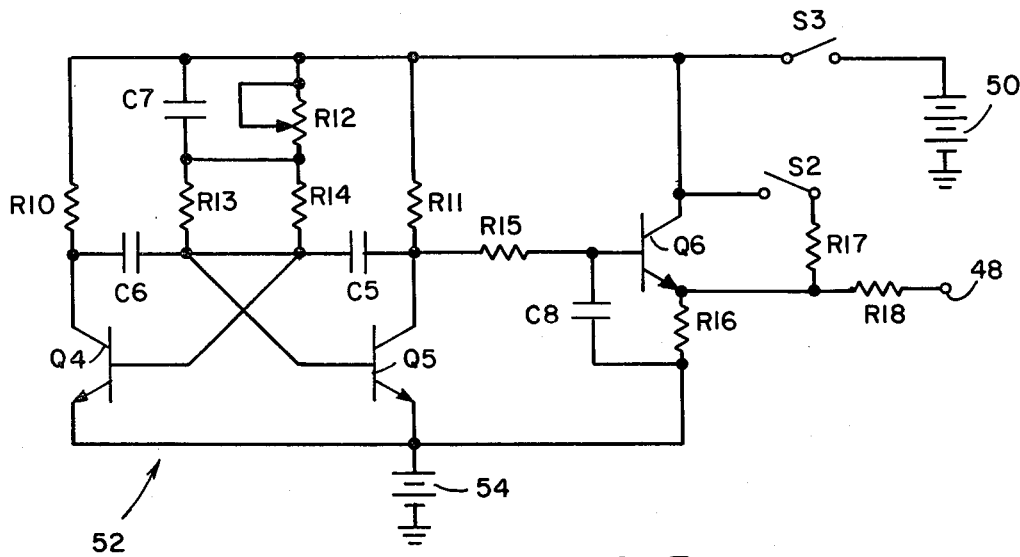
FIG. 5 is a detailed schematic of an alternative power supply to the rate potentiometer of FIG. 3 to provide for bursts of pulses or a periodically varying pulse rate.

An alternative power supply to the rate control potentiometer 16 of FIG. 3 is shown in FIG. 5. In use, the potentiometer 16 is disconnected from the switch S1 in FIG. 3, and power is supplied to that potentiometer from pin 48 in the circuit of FIG. 5. This alternative power supply has its own 7.5 volt battery 50 which, when switch S 3 is closed, drives an astable multivibrator circuit 52. That circuit provides 50% duty-cycle pulses to a buffer amplifier including transistor Q6. By adjustment of potentiometer R12, the period of the resultant pulse train is from 4 to 12 seconds.

With the switch S2 in the OPEN position, the voltage level at output pin 48 switches from the 2.8 volts of the power supply 54 when transistor Q6 is OFF, to 5.8 volts when transistor Q6 is ON. The 2.8 volts is insufficient to trigger the astable multivibrator 14 in the circuit of FIG. 3. Thus, during that half of the cycle of the signal on line 48, no stimulation is provided to the patient. During the 2 to 6 second interval that the output on line 48 is high, the astable multivibrator 14 is enabled through the potentiometer 16. Adjustment of the potentiometer 16 determines the firing rate of the multivibrator 14 during that 2 to 6 second interval. The multivibrator fires many times during the interval and provides stimulation through the FIG. 1 electrodes 34 and 36. If the astable multivibrator 14 is connected directly to the trigger circuit 18, this alternative power supply provides for pulse bursts of a constant frequency to the patient. If, however, the random generator 40 is connected between pins A and B, continuously varying pulses are applied during the intervals that the multivibrator 14 is enabled.

When switch S2 of FIG. 5 is closed, the battery 50 is connected across a voltage dividing circuit R16, R17. That circuit provides a 4.8 volt output on pin 48 when transistor Q6 is turned OFF. When the transistor Q6 is turned ON, the full 5.8 volts is applied to the pin 48. The 4.8 volts applied to the astable multivibrator 14 during the interval that transistor Q6 is OFF is sufficient to allow for firing of the multivibrator 14, but the firing rate is less than when the full 5.8 volts is applied. Thus, as transistor Q6 switches ON and OFF with pulses from the astable multivibrator 52, the multivibrator 14 fires first at one rate and then at another lower rate. The pulses applied to the patient have a periodically varying rate if a direct connection is made between pins A and B of FIG. 1. If random generator 40 is connected in the circuit an even more random pulse train is applied to the patient.

The capacitor C8 of FIG. 5 slows the rise time of the output at pin 48 and thus causes a gradual rate increase each time the transistor Q6 turns ON.

The following values have been found suitable for the circuit elements in the circuit of FIG. 5:

R10, R11: 47 K ohm
R12: 1 M ohm
R13, R14: 330 K ohm
R15: 4; K ohm
R16: 4.7 K ohm
R17: 15 K ohm
R18: 7.5 K ohm
C5, C6: 4.7 μf
C7, C8: 1.0 μf While the invention has been particularly shown and described with reference to preferred embodiments thereof, it will be understood by those skilled in the art that various changes in form and details may be made therein without departing from the spirit and scope of the invention as defined by the appended claims. Further, it is believed that the varying pulse rate will have a beneficial effect in the treatment of pain using the claimed transcutaneous nerve stimulator.

We claim:
1. A transcutaneous nerve stimulator comprising:
   a digital electronic pseudorandom pulse generator and a current source for providing a series of electrical current pulses of generally trapezoidal and monophasic waveform, to mimic the typical physiological waveforms, at a continuously varying rate, the pulses being substantially identical to each other in amplitude and duration; and a pair of electrodes, each electrode being connectable to the outer skin of a body to apply the electrical pulses across a portion of the body and thereby deliver the pulses through a nervous system to the brain.

2. A transcutaneous nerve stimulator as claimed in claim 1 wherein the electrical pulses have a base pulse rate in the order of the alpha rate.

3. A transcutaneous nerve stimulator comprising:
a variable frequency pulse source;
a digital electronic pseudorandom pulse generator comprising a shift register circuit and a logic circuit, said pulse generator being responsive to the output of the variable frequency pulse source to shift input pulses from said variable frequency pulse source through said shift register circuit at a rate determined by said input pulses from said variable frequency pulse source, said shifted input pulses being generated by logic circuitry responsive to outputs of said shift register circuit, thereby to provide a series of constant duration and amplitude pseudorandom electrical pulses at a varying rate;

a current source responsive to the pseudorandom electrical pulses to provide pseudorandom electrical current pulses which are trapezoidal and monophasic to mimic the typical phsysiological waveforms; and a pair of electrodes, each electrode being connectable to the outer skin of a body to apply the pseudorandom electrical current pulses across a portion of the body and thereby deliver the pseudorandom pulses through the nervous system to the brain.

4. A transcutaneous nerve stimulator as claimed in claim 3 wherein said variable frequency pulse source has a pulse rate in the order of the alpha rate.

5. A transcutaneous nerve stimulator as claimed in claim 1 or 3 wherein a train of electrical pulses has a net zero DC level.

6. A transcutaneous nerve stimulator as claimed in claim 1 or 3 further including means for adjusting the pulse width of the electrical pulses.

7. A transcutaneous nerve stimulator of claim 1 or 3 further comprising means for adjusting the current amplitude of the electrical pulses.

* * * * *